(12) United States Patent
Lilga et al.

(10) Patent No.: US 7,687,661 B2
(45) Date of Patent: *Mar. 30, 2010

(54) METHOD FOR CONVERSION OF β-HYDROXY CARBONYL COMPOUNDS

(75) Inventors: Michael A. Lilga, Richland, WA (US); James F. White, Richland, WA (US); Johnathan E. Holladay, Kennewick, WA (US); Alan H. Zacher, Kennewick, WA (US); Danielle S. Muzatko, Kennewick, WA (US); Rick J. Orth, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 108 days.

This patent is subject to a terminal disclaimer.

(21) Appl. No.: 11/377,096

(22) Filed: Mar. 15, 2006

(65) Prior Publication Data

US 2007/0219391 A1    Sep. 20, 2007

(51) Int. Cl.
C07C 67/30 (2006.01)
(52) U.S. Cl. .................. 560/212; 560/211; 560/185
(58) Field of Classification Search ............ 560/212, 560/211, 185
See application file for complete search history.

(56) References Cited

U.S. PATENT DOCUMENTS

| | | | |
|---|---|---|---|
| 2,361,036 A | 10/1944 | Kung et al. | |
| 2,375,005 A | 5/1945 | Kung | |
| 2,415,645 A | 2/1947 | Lithtenwalter et al. | |
| 2,469,701 A | 5/1949 | Redmon et al. | |
| 2,508,279 A | 5/1950 | Lichtenwalter et al. | |
| 2,548,156 A | 4/1951 | Gresham et al. | |
| 2,623,070 A | 12/1952 | Jansen et al. | |
| 2,734,077 A | 2/1956 | Smith | |
| 2,749,355 A * | 6/1956 | Jones | 548/400 |
| 2,806,878 A | 9/1957 | Luberoff et al. | |
| 2,859,240 A | 11/1958 | Holmen et al. | |
| 3,471,451 A | 10/1969 | Moore et al. | |
| 3,562,320 A | 2/1971 | Woodward et al. | |
| 3,666,805 A | 5/1972 | Volker et al. | |
| 3,670,020 A | 6/1972 | Moore | |
| 3,974,207 A * | 8/1976 | Szelejewski et al. | 560/212 |
| 4,237,067 A | 12/1980 | Küster et al. | |
| 4,263,293 A | 4/1981 | Sundeen et al. | |
| 4,528,350 A | 7/1985 | Goossens et al. | |
| 4,536,599 A | 8/1985 | Masuko et al. | |
| 4,729,978 A | 3/1988 | Sawicki | |
| 4,786,756 A | 11/1988 | Paparizos et al. | |
| 4,820,872 A | 4/1989 | Farrar et al. | |
| 5,250,729 A | 10/1993 | Abe et al. | |
| 5,321,156 A | 6/1994 | Behr et al. | |
| 5,371,273 A | 12/1994 | Shima et al. | |
| 5,739,379 A | 4/1998 | Shima et al. | |
| 2002/0055650 A1 | 5/2002 | Hidaka et al. | |
| 2005/0222458 A1 | 10/2005 | Craciun | |

FOREIGN PATENT DOCUMENTS

| | | |
|---|---|---|
| CN | 1594263 A | 3/2005 |
| DE | 573 724 C | 4/1933 |
| DE | 729 342 C | 12/1942 |
| DE | 954 596 C | 12/1956 |
| DE | 2819735 | 9/1982 |
| EP | 1 205 471 A1 | 5/2002 |
| GB | 744582 | 2/1956 |
| JP | 2000-264859 | 9/2000 |
| WO | WO 02/090312 A1 | 11/2002 |
| WO | WO 03/082795 A2 | 10/2003 |
| WO | WO 2005/095320 A1 | 10/2005 |

OTHER PUBLICATIONS

PCT/US2006/012696—PCT International Search Report and Written Opinion of the International Searching Authority (Jan. 19, 2007).
PCT/US2006/012697—PCT International Search Report and Written Opinion of the International Searching Authority (Jan. 19, 2007).
Campi, et al., Synthesis and Structure of (E)-3-Phenylmethylene-2-oxetanone: Comments on the Stability of Methylene B-Lactones, Sep. 1990, pp. 855-856.
Von F. Beilstein., Ueber die Umwandlung der Glycerinsaure in Acrylsaure, American Chemical Society, 1882, vol. 1226, pp. 366-376 (No English translation).
Hoffmann Berichte 15 (1882) pp. 977-984 (No English translation).
Kundig, Chemie und Pharmacie, 105, (1858) pp. 277-278 (No English translation).
A.J. Grant, et al., A Study of Some Rare Earth Compounds, JACS, 39, (1917), pp. 933-937.

(Continued)

*Primary Examiner*—Peter G O'Sullivan
*Assistant Examiner*—Sudhakar Katakam
(74) *Attorney, Agent, or Firm*—James D. Matheson (57) ABSTRACT

A process is disclosed for conversion of salts of β-hydroxy carbonyl compounds forming useful conversion products including, e.g., α,β-unsaturated carbonyl compounds and/or salts of α,β-unsaturated carbonyl compounds. Conversion products find use, e.g., as feedstock and/or end-use chemicals.

23 Claims, 6 Drawing Sheets

OTHER PUBLICATIONS

Frederick L. Dunlap, JACS, 24, (1902) pp. 758-763 (No English Translation).
J. Prakt. Chem 31:2 (1885) pp. 363-382.
Verley Bull Soc. Chim, 9:3 (1893) pp. 691-692 (No English Translation).
Coleman, et al., Acetamide, Organic Synthesis, vol. III, 1956, pp. 3-5.
Mitchell, et al., The Preparation of Aliphatic Amides, JACS, 53, (1931), pp. 1879-1883.
Phelps, Am. J. Sci 24:4, (1907) pp. 429-432.
Noyes, et al., Catalysis of the Formation and Dyrolysis of Acetamide by Acetic Acid, JACS, 44, (1922), pp. 2286-2295.
A.W. Ralston, Solubilities of Some Normal Aliphatic Amides, Anilides, and N,N-Diphenylamides, JOC, 8, (1943) pp. 473-488.
Yokokawa, et al., Tetrahedron Letters 43 (2002) pp. 8673-8677.
Yokokawa, et al., Tetrahedron Letters 43 (2002) pp. 8679-8682.
Bartoli, et al., Organic Letters 2, (2002) pp. 1791-1793.
Goodall, et al., A New and Effcient Preparation of a,B-Dehydramino Acids, Tetrahedron Letters, vol. 36, No. 18, pp. 3259-3260.
Noyce, et al., Carbonyl Reactions, JACS 80, (1958) pp. 5539-5543.
Kon, et al., The Dehydration of B-Hydroxy-esters, J. Chem. Soc (1932), pp. 2461-2463.
Gibson, et al., Synthesis and structural analysis of dehydrophenylalanine cyclophanes, Chem. Communication, (2002), 17, pp. 1938-1939.
Parrick, et al., Four-Membered Ring Systems, Progress in Heterocyclic Chemistry, 10 (1998) pp. 70-86.
Andrezej Gawecki, Matrix Theory of Elastic-Plastic-Slackened Structures, Bulletin of the Polish, Academy of Sciences, vol. 37, No. 3-4, 1989, pp. 141-145.

Adam, et al., Sterospecific Introduction of Double Bonds via Thermolysis of B-Lactones, JACS, 94, (1972), pp. 2000-2006.
Yamana, et al., Chemical and Pharmaceutical Bulletin 20, (1972), pp. 1217-1229.
H. Li, et al., Peptide Science, 7, (2001) pp. 82-91.
Okeley, et al., Facile Chemoseletive Synthesis of Dehydroalanine-Containing Peptides, Organic Letters, 2, (2000), pp. 3603-3606.
Spetzler, et al., Journal of Peptide Science, 5, (1999) pp. 582-592.
Wolfe, et al., Dept. of Chem, Can J. Chem. 72, pp. 1066-1075 (1993).
Pansare, et al., Organic Syntheses 70, (1992), pp. 1-9.
Pansare, et al., Organic Syntheses 70 (1992), pp. 10-17.
Arnold, et al., Polymer-Supported Alkyl Axodicarboxylates for itsunobu Reactions, JACS, 111, (1989) pp. 3973-3976.
Arnold, et al., JACS, 109, (1987) pp. 4649-4659.
Ramer, et al, Can. J. Chem. 64., (1986), pp. 706-713.
Arnold, et al., J. Am. Chem. Soc. (1985), 107, pp. 7105-7109.
Alexandre, et al., Tetrahedron 56 (2000) pp. 3921-3926.
Sliedreg, et al., Tetrahedron Letters, 37, (1996), pp. 4237-4240.
Gokarn, et al, 3-Hydroxypropionic Acid, Polymer Preprints, vol. 44, No. 2, (2003), Amer. Chem Society, p. 572.
Gokarn, et al, Abstract of Papers (238), 226th ACS National Meeting, 2003.
Gresham, et al., B-Propiolactone, JACS, (1948) V. 70, pp. 998-999.
Piccolo, et al., (1994) Elsevier Science, pp. 329-334.
Kon, et al., The Dehydration of B-Hydroxy-esters, J. Chem Soc. (1932), pp. 2461-2463.
Crawford et al., The a,b,y-Triphenylbutyric Acids and Related Compounds, Journal of American Chemical Society, 1944, vol. 66, pp. 2010-2013.

* cited by examiner

METHOD FOR CONVERSION OF β-HYDROXY CARBONYL COMPOUNDS

This invention was made with Government support under Cooperative Research and Development Agreement (CRADA) Number PNNL-217 between Battelle, as operator of Pacific Northwest National Laboratory under U.S. Department of Energy Contract DE-AC0676RLO-1830, and Cargill, Inc. The Government has certain rights in the invention.

FIELD OF THE INVENTION

The present invention relates generally to a method for conversion of salts of β-hydroxy carbonyl compounds to conversion products including, e.g., salts of α,β-unsaturated carbonyl compounds. Conversion products find use, e.g., as feedstock and/or end-use chemicals.

BACKGROUND OF THE INVENTION

While many chemical intermediates (e.g., lactic acid and succinic acid) can be produced via bio-derived processes such as fermentation, in order to match the scale, flexibility, and efficiency of the petrochemical industry, the bioproducts industry must develop additional chemical building blocks that are versatile and competitive. For example, acrylic acid is a prominent chemical that is polymerized into a broad range of versatile chemicals and resins, including plastics and hydrogels. Acrylic acid is also a co-polymer component in aerosol hair sprays and finds application as a foam stabilizer in shampoos. In medicine and dentistry, acrylic acid is used in the manufacture of dental plates, artificial teeth, and orthopedic cements. Acrylic acid is also a chemical intermediate used in the formation of acrylates which find application in polymer solutions for coating applications, emulsion polymers, paint formulations, and paper coatings. And, esters of acrylic acid play major roles in coatings, textiles, adhesives, paper, and plastics.

Accordingly, there remains a need to develop processes for production of such chemical intermediates from which a host of useful products can be made.

SUMMARY OF THE INVENTION

In one aspect, the invention is a process comprising the steps of providing a material comprising a salt of a β-hydroxy carbonyl compound to a reactor and/or one or more stages thereof at a rate and a temperature whereby said material dehydrates; and wherein the material is converted to one or more reaction products selected from the group consisting of acrylates, acrylate salts, acrylamide, polymers thereof, and/or combinations thereof at high yield by substantially continuous removal of water.

In one embodiment, the material is a melt of a salt of a β-hydroxy carbonyl compound.

In another embodiment, the salt of the β-hydroxy carbonyl compound is selected from the group of alkali, alkaline earth, transition metal, precious metal, ammonium, or combinations thereof.

In another embodiment, the β-hydroxy carbonyl compound is selected from the group of 3-hydroxypropionate, 3-hydroxypropionate ester dimers, 3-hydroxypropionate ether dimers, or combinations thereof.

In another embodiment, a catalyst is added to the reactor and/or one or more stages thereof for conversion of the material.

In another embodiment, the catalyst is a dehydration catalyst.

In another embodiment, the catalyst is selected from the group of solid oxides, solid acids, acidic catalysts, weakly acidic catalysts, strongly acidic catalysts, basic catalysts, ion-exchange resins, acidic gases, basic gases, or combinations thereof.

In another embodiment, the solid oxide catalyst is selected from the group consisting of $TiO_2$, $ZrO_2$, $Al_2O_3$, $SiO_2$, $ZnO_2$, $SnO_2$, $WO_3$, $MnO_2$, $Fe_2O_3$, $SiO_2/Al_2O_3$, $ZrO_2/WO_3$, $ZrO_2/Fe_2O_3$, $ZrO_2/MnO_2$, or combinations thereof.

In another embodiment, the acidic or weakly acidic catalyst is selected from the group consisting of titanic acids, metal oxide hydrates, metal sulfates, metal oxide sulfates, metal phosphates, metal oxide phosphates, carbon dioxide, mineral acids, carboxylic acids, acidic resins, acidic zeolites, clays, ammonium salts thereof, or combinations thereof.

In another embodiment, the acidic catalyst is selected from the group of Ti-0720®, $SiO_2/H_3PO_4$, fluorinated $Al_2O_3$, $Nb_2O_3/PO_4^{-3}$, $Nb_2O_3/SO_4^{-2}$, $Nb_2O_5 \cdot H_2O$, phosphotungstic acids, phosphomolybdic acids, silicomolybdic acids, silicotungstic acids, carbon dioxide, PVPH$^+$Cl$^-$®, ECS-3®, or combinations thereof.

In another embodiment, the basic catalyst is selected from the group of ammonia, polyvinylpyridine, metal hydroxides, $Zr(OH)_4$, or amines of the form $NR_1R_2R_3$, wherein $R_1$, $R_2$, and $R_3$ are independently selected from the group consisting of H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof.

In another embodiment, the material is mixed in a calciner/extruder, Auger reactor, or a stirred tank.

In another embodiment, the material is partially converted in a first stage of a reactor and finally converted in a second stage of a reactor in the presence of a catalyst in one or both of the first or second stages of a reactor.

In another embodiment, a first stage of a reactor comprises mixing in a slurry tank or a stirred tank and the second stage of a reactor comprises mixing in a calciner/extruder, Auger reactor, or a stirred tank.

In another embodiment, the calciner/extruder is a rotary calciner/extruder.

In another embodiment, the calciner/extruder further comprises use of a member selected from the group of stirred tank, rotary calciner, Auger reactor, extruder, evaporator, evacuator, or combinations thereof.

In yet another embodiment, one or more reaction products converted in a reactor and/or one or more stages thereof are separated from a catalyst when present by rehydrating in water and recovered.

In another embodiment, the material is mixed with a catalyst for conversion of the material in a slurry reactor or stirred tank followed by spray-drying to remove water.

In another embodiment, an inhibitor is added to a material in a reactor to minimize polymer formation.

In another embodiment, one or more reaction products are collected from a reactor and/or one or more stages thereof in a substantially neat form.

In another embodiment, conversion of a material is in the range from about 60 percent to about 100 percent.

In another embodiment, one or more reaction products are recovered at a molar yield in the range from about 70% to about 100%.

In another embodiment, temperature for conversion of a material is selected in the range from about 100° C. to about 250° C.

In another embodiment, temperature for conversion of a material is selected in the range from about 180° C. to about 220° C. at atmospheric pressure.

In another embodiment, temperature for conversion of a material is selected in the range from about 100° C. to about 180° C. with a partial vacuum selected in the range from about 20 mm Hg to about 200 mm Hg.

BRIEF DESCRIPTION OF THE DRAWINGS

A more complete appreciation of the invention will be readily obtained by reference to the following description of the accompanying drawings in which like numerals in different figures represent the same structures or elements.

DETAILED DESCRIPTION OF THE INVENTION

While the present invention is described herein with reference to the preferred embodiments thereof, it should be understood that the invention is not limited thereto, and various alternatives in form and detail may be made therein without departing from the spirit and scope of the invention.

The present invention relates generally to a method for conversion of salts of β-hydroxy carbonyl compounds as a source material to conversion products including, e.g., α,β-unsaturated carbonyl compounds and/or salts of α,β-unsaturated carbonyl compounds, including, e.g., acrylic acid [CAS No. 79-10-7], acrylates, and acrylamide [CAS No. 79-06-01] at high molar yield. The term "source material" or "material" as used herein refers to one or more β-hydroxy carbonyl compounds introduced to a reactor giving rise to the desired conversion products. The term encompasses all associated reagents and/or chemical constituents introduced therewith including, e.g., solvents, inhibitors, stabilizers, or the like. In one embodiment, a source material is composed substantially of a salt of a β-hydroxy carbonyl compound. The salt is selected from the group of alkali, alkaline earth, transition metal, precious metal, ammonium, or combinations thereof. The β-hydroxy carbonyl compound is selected from the group of 3-hydroxypropionate, 3-hydroxypropionate ester dimers, 3-hydroxypropionate ether dimers, or combinations thereof. No limitations are intended.

The term "conversion" as used herein refers to the quantity of a source material consumed in a specified reaction as a function of the quantity of the source material introduced to a reactor or a stage thereof, as defined by equation [1]:

$$\text{Conversion} = \left(\frac{\text{Moles Source Material Consumed}}{\text{Moles Source Material Fed to Reactor}}\right) \quad [1]$$

The term "partial conversion" as used herein refers to conversion of a source material in a reactor or stage thereof wherein quantities of conversion products are determined by reaction equilibria in the selected medium. For example, partial conversion in aqueous media is on the order of about 50%, but is not intended to be limiting, as equilibria may be controlled as described herein providing conversion yields above the equilibrium controlled maximum.

The term "final conversion" or "finally converted" as used herein refers to conversion of a source material above its "partial conversion" or equilibrium-controlled maximum. Final conversion may be achieved as described herein, e.g., in a reactor or stage coupled to, or secondary with, a primary equilibrium-controlled reactor or stage.

The term "conversion products" as used herein refers to any of the one or more reaction products generated in conjunction with the apparatus', processes, and/or systems described herein that find use as feedstock and/or end-use chemicals, and/or that play a reactive and/or chemical role in the apparatus, processes, and/or systems described. The terms "conversion products" and "reaction products" are used synonymously. No limitations are intended.

The term "molar selectivity" as used herein refers to the quantity (moles) of reaction (or conversion) products formed as a ratio of the moles of source material consumed, determined from equation [2]:

$$\text{Molar Selectivity} = \left(\frac{\text{Moles of Product Formed}}{\text{Moles of Source Material Consumed}}\right) \quad [2]$$

The term "molar yield" as used herein is defined by equation [3] as the moles of reaction (or conversion) products formed as a ratio of the moles of a source material introduced (fed) to a reactor:

$$\text{Molar Yield} = \left(\frac{\text{Moles of Product Formed}}{\text{Moles of Source Material Fed to Reactor}}\right) \quad [3]$$

The term "high molar yield" as used herein refers to a molar yield of greater than or equal to about 70 percent.

The term "flow rate" as used herein is defined as the weight-hourly space velocity (WHSV), given by equation [4]:

$$\text{Flow Rate} = \left(\frac{\text{g Source Material}}{\text{g Catalyst}}\right)/\text{hour} \quad [4]$$

Reactions involved in conversion of source materials to products of interest include, but are not limited to, amination, deamination, dehydration, etherification, esterification, hydrolysis, or combinations thereof. The person of skill in the art will appreciate that processes as set forth herein for producing and converting specific moieties, and their chemical derivatives and intermediates, will occur at a variety of conversion rates, selectivities, and/or molar yields. All conversions as will be considered significant by the person of skill in the art are within the scope and spirit of the invention. No limitations are hereby intended.

In one embodiment, the invention provides for continuous production of, e.g., acrylic acid as a conversion product of a source material comprising a β-hydroxy carbonyl compound. β-Hydroxy carbonyl compounds include, but are not limited to, 3-hydroxypropionic acid, substituted 3-hydroxypropionic acids, 3-hydroxypropionic esters, 3-hydroxypropionic ester dimers, 3-hydroxypropionic acid ethers, 3-hydroxypropionic acid ether dimers, 3-hydroxypropionic acid salts, 3-hydroxypropionic amides, 3-aminopropionic acids, 3-hydroxypropionaldehydes, or combinations thereof.

Substituted 3-hydroxypropionic acids comprise the group of compounds having the general form:

where X and Y are independently selected from the group consisting of H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof.

3-Hydroxypropionic acid ester dimers, also known as 3-Hydroxypropionic acid acrylate ester dimers, comprise the group of compounds having the general form:

where X and Y are independently selected from the group consisting of H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof.

3-Hydroxypropionic acid ether dimers, also known as 3-Hydroxypropionic acid acrylate ether dimers, comprise the group of compounds having the general form:

where X and Y are independently selected from the group consisting of H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof.

3-Hydroxy-propionic amides comprise the group of compounds having the general form:

where X and Y are independently selected from the group consisting of H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof, and where $R_1$ and $R_2$ are independently selected from the group consisting of H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof.

3-Amino-propionic acids comprise the group of amino acid compounds having the general form:

where X and Y are independently selected from the group consisting of H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof, and where $R_1$ and $R_2$ are independently selected from the group consisting of H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof.

3-Hydroxypropionic propianaldehydes comprise the group of compounds having the general form:

where X and Y are independently selected from the group consisting of H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof.

Reaction or conversion products derived from source materials comprising β-hydroxy carbonyl compounds include the family of α,β-unsaturated carbonyl compounds having the general form:

where X and Y are independently selected from the group consisting of H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof; functional group R includes members independently selected from H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof. Stereochemistry about the double bond is not shown, but is not intended to be limiting. Reaction products comprising α,β-unsaturated carbonyl compounds include, but are not limited to, e.g., acrylic acid, methacrylic acid, salts thereof, esters thereof, acrolein, or combinations thereof. In other processes, reaction products include formation of acrylates, acrylamide, polymers thereof, or combinations thereof. In still yet other processes, reaction products include formation of acrylic acid, methacrylic acid, amides thereof, salts thereof, acrolein, or combinations thereof. However, reaction products are not limited thereto. For example, water is easily generated from dehydration reactions occurring within the reactor. Thus, no limitations are intended.

Catalysts

Any catalyst capable of assisting in the conversion of a source material to desired end-use and/or reaction products may be selected without limitation. Catalysts are selected from classes including, e.g., acidic, neutral, or basic depending on desired reaction conditions promoted and respective conversion performance, as will be understood by those of skill in the art. For example, some reaction conditions will involve low pH conditions, e.g., when the source material is a carboxylic acid. In this case acidic catalysts are preferred. When the source material comprises, e.g., a carboxylic ester or a salt, reaction conditions will be of a neutral pH and catalysts may be selected from any appropriate class as long as the catalyst has sufficient activity. In conditions where ammonia is added, or e.g., a compound comprising an ammonium salt is present, basic catalysts are preferred. In short, pH suitable catalysts can be employed depending on reaction conditions.

Catalysts include, but are not limited to, solid oxides, solid acids, acidic catalysts, weakly acidic catalysts, strongly acidic catalysts, basic catalysts, ion-exchange resins, acidic gases, basic gases, or combinations thereof.

Solid oxide catalysts include, but are not limited to, e.g., $TiO_2$, $ZrO_2$, $Al_2O_3$, $SiO_2$, $ZnO_2$, $SnO_2$, $WO_3$, $MnO_2$, $Fe_2O_3$, $V_2O_5$, $SiO_2/Al_2O_3$, $ZrO_2/WO_3$, $ZrO_2/Fe_2O_3$, $ZrO_2/MnO_2$, or combinations thereof.

Acidic or weakly acidic catalysts further include titania catalysts, $SiO_2/H_3PO_4$ catalysts, fluorinated $Al_2O_3$ (e.g., $Al_2O_3.HF$) catalysts, $Nb_2O_3/PO_4^{-3}$ catalysts, $Nb_2O_3/SO_4^{-2}$ catalysts, $Nb_2O_5.H_2O$ catalysts, phosphotungstic acid catalysts, phosphomolybdic acid catalysts catalysts, silicomolybdic acid catalysts, silicotungstic acid catalysts, carbon dioxide, acidic polyvinylpyridine hydrochloride catalysts, hydrated acidic silica catalysts, and combinations thereof. A preferred titania catalyst is Ti-0720® (Engelhard, Iselin, N.J., USA). A preferred polyvinylpyridine hydrochloride catalyst is PVPH$^+$Cl$^-$® (Reilly, Indianapolis, Ind., USA). A preferred hydrated acidic silica catalyst is ECS-3® (Engelhard, Iselin, N.J., USA). No limitations are intended.

Basic catalysts include, but are not limited to, e.g., ammonia, polyvinylpyridine, metal hydroxides, $Zr(OH)_4$, and amines of the form $NR_1R_2R_3$, where $R_1$, $R_2$, and $R_3$ are independently selected from the group of side chain or functional groups including, but not limited to, e.g., H, hydrocarbons containing from 1 to 20 carbon atoms, heteroatom substituted hydrocarbons containing from 1 to 20 carbon atoms, alkyl and/or aryl groups containing from 1 to 20 carbon atoms, or combinations thereof. No limitations are intended.

Solvents

Solvents include, but are not limited to, donor solvents, non-donor solvents, non-protic solvents, acceptor solvents, and protic solvents. Protic solvents include, e.g., alcohols, water, and combinations thereof. Alcohols include, but not limited to, alkanols composed of from 1 to 20 carbon atoms (e.g., methanol, ethanol, etc). No limitations are intended.

A packed, fixed-bed reactor of a continuous flow design will now be described in reference to FIG. 1.

Figure 1:
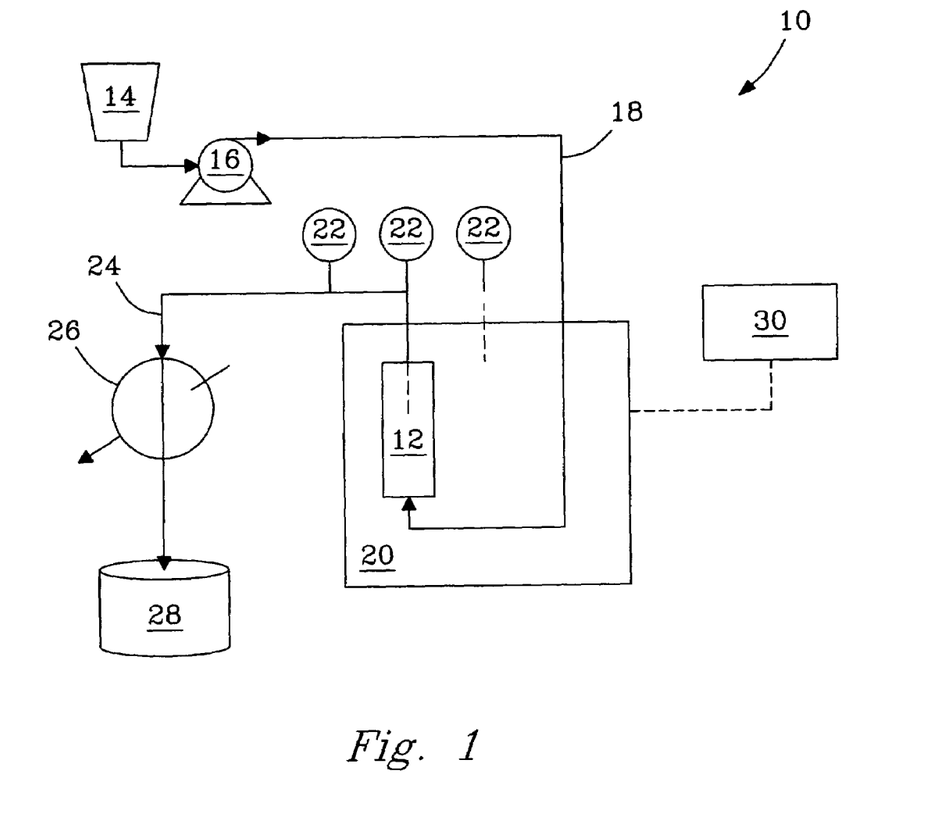
FIG. 1 illustrates a fixed-bed reactor or reactor system for practicing the process of the invention.

FIG. 1 illustrates a reactor system 10 for practicing the process of the invention, according to one embodiment of the invention. Appropriate scale-up of system components can be effected within the scope of the present invention suitable for industrial and/or manufacturing applications. All equipment and system configurations as will be implemented by the person of skill in the art are incorporated herein. No limitations are intended. System 10 comprises a reactor 12, e.g., of a catalyst bed type, coupled to a feed source 14 for introducing a source material (i.e., "the material") to reactor 12, a pumping system 16 for moving materials and fluids in/out of reactor 12. Reactor 12 is located within a heating source 20, e.g., a fluidized heating bed, furnace, or other heating source. Source material comprises any of a variety of β-hydroxy carbonyl compounds, including, but not limited to, e.g., 3-hydroxypropionic acid, which is introduced to reactor 12 from source 14 at a flow rate defined, e.g., as a weight hourly space velocity (WHSV) optimized for conversion of the material in reactor 12. In particular, flow rate is selected in the range from about 0.05 WHSV to about 10 WHSV. More particularly, flow rate is in the range from about 0.2 WHSV to about 0.4 WHSV. However, flow rates are not limited thereto. Any flow rate optimizing conversion of the selected source material in reactor 12 or other reactor systems described herein which may be employed is within the scope of the invention. For example, rates will depend in part on reactor design (e.g., whether bench-scale, pilot-scale, commercial-scale, continuous-flow, batch, etc.), quantity of catalyst employed, reactor temperatures, as well as other associated reactor conditions and parameters. Thus, no limitations are hereby intended.

In the instant embodiment, reactor 12 is mounted within heating source 20 coupling to a pump or other pumping system 16 via ½-inch stainless steel tubing 18, but is not limited thereto. Pumping system 16 introduces source material to the bottom of reactor 12, the material flowing up through reactor 12 but is again not limited thereto. Temperature is measured with thermocouples 22 or other suitable temperature indicating devices placed at various locations within system 10, e.g., of heating source 20 and of reactor 12. In the instant embodiment, conversion products are collected as an effluent stream from the top of reactor 12 in a collection vessel 28 coupled to reactor 12 via 1/16-inch stainless steel tubing 24. In an alternate configuration, conversion products are distilled from reactor 12 into individual product streams given vapor pressure and/or boiling points differences between the various reaction products of interest. Reactor 12 is further configured with an optional by-pass loop 26 used as a sampling line for taking process samples. No limitations are hereby intended. Devices and processes occurring within system 10 may be automated by linking with a computer 30. All configurations as will be envisioned and/or implemented by those of skill in the art are within the scope of the invention.

System 10 operates at atmospheric pressure at a temperature above the boiling temperature of water, permitting a feed material in a condensed form to be used. Direction of flow of the source material within and through system 10 and/or reactor 12 is not limited. For example, source material may be introduced to reactor 12 from a point entering anywhere along the vertical length (e.g., center and side) of reactor 12, e.g., whereby solvents when used will flow downward through reactor 12 for collection and recycle from the bottom of reactor 12 and reaction products will distill individually from the top of reactor 12 for collection. Products are removed as they are formed retarding polymerization within reactor 12.

Various catalysts may be employed in reactor 12, as described herein, or operated in the absence of catalysts, permitting substantial control of reaction conditions and operation parameters. For example, catalysts may be introduced to reactor 12 prior to introduction of a source material or be introduced simultaneously with the source material in continuous mode operation. No limitations are hereby intended. For example, other components and devices may be incorporated within system 10 including, but not limited to, temperature and pressure controllers and devices, transfer systems (e.g., fluids, solvents, conversion products, reagents, and the like), and/or associated equipment including those for collecting and storing data as will be contemplated by the person of skill in the art. Further, as will be understood by those of skill in the art, components and devices within system 10 may be controlled and/or interfaced in conjunction with computers and/or other associated electronic devices without reservation, e.g., for collecting data, controlling pressure and temperature, and the like. No limitations are hereby intended.

Conversion involves heating the material in the presence of a catalyst at a temperature and residence time with the catalyst yielding various reaction products.

Molar yields for reaction products are achieved in the range up to about 100 percent. More particularly, molar yields are in the range from about 80 percent to about 100 percent. Most particularly, yields are in the range from about 90 percent to about 100 percent. High yields for reaction and/or conversion products of interest are obtained at least in part by removing at least one of the conversion products upon formation thereby controlling and/or limiting further reactions and/or chemistries including, but not limited to, e.g., dimerization, oligomerization, re-hydration. In one example, high yield of acrylic acid from conversion of 3-hydroxypropionic acid is obtained by removing acrylic acid (e.g., by vaporization) as it is formed thereby controlling reaction equilibria and limiting potential for dimerization, oligomerization, or re-hydration (i.e., formation of the source material again). Choice of reaction temperature has also proven important to process yields. In particular, reaction temperatures are selected in the range from about 90° C. to about 250° C. More particularly, reaction temperatures are selected in the range from about 90° C. to about 180° C. in conjunction with a partial vacuum in the range from 20 mm Hg to about 200 mm Hg. Alternatively, temperatures are selected in the range from about 180° C. to about 200° C. at atmospheric pressure. In an alternate configuration, temperatures are selected in the range from about 200° C. to about 500° C. in conjunction with a pressure in the range from about 20 psig to about 500 psig.

Various reactors may be employed without departing from the scope of the invention, including, but not limited to, trickle-bed, fixed-bed, fluidized bed, stirred tank, continuous stirred tank, ebulating bed, membrane, Berty, plug-flow, bubble-column, reactive-distillation column, or combinations thereof. In addition, various and multiple reactor configurations may be employed without limitation. In but one example of an industrial scale design, multiple and/or various reactors may be arranged, e.g., side by side, in conjunction with, e.g., a centralized heating source for heating reactors and providing for heat transfer, a centralized material source for supplying source material to the reactor at a suitable flow rate (WHSV), the industrial scale design providing for removal of reaction (or conversion) products as described herein whereby high product yields are obtained.

Figure 2:
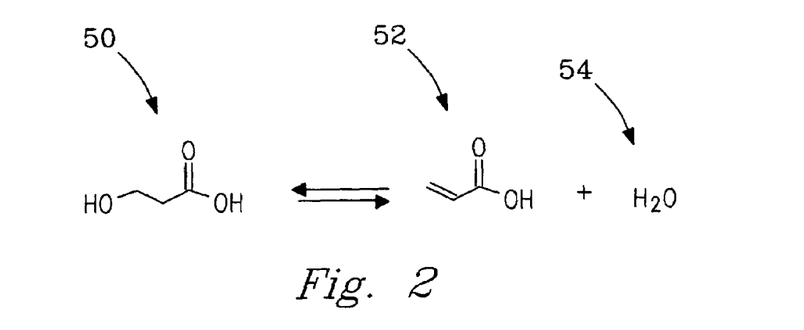
FIG. 2 illustrates a generalized reaction process for conversion of a source material comprising β-hydroxy carbonyl compounds yielding acrylic acid as a reaction product, according to an embodiment of the invention.

FIG. 2 illustrates a generalized reaction process for conversion of β-hydroxy carbonyl compounds in a source material 50 yielding acrylic acid, according to an embodiment of the invention. Sources for β-hydroxy carbonyl compounds include, but are not limited to, e.g., fermentation, other chemical processes, or the like. Source material 50 can include monomers, dimers, oligomers, or combinations thereof. Further, as described herein, various solvents may be added, but are not mandatory. For example, in the instant embodiment, the source material 50 comprises water, but the invention is not limited thereto. No limitations are intended.

In the instant embodiment, source material 50 comprising, e.g., 3-hydroxypropionic acid, is converted via dehydration reaction to acrylic acid 52 plus water 54. Source material 50 is provided under generally continuous flow to reactor 12, packed with, e.g., a dehydration catalyst in a fixed-bed configuration. Material 50 is heated in the presence of the catalyst at a temperature and residence time sufficient to dehydrate the material in contact with the catalyst, yielding the desired reaction product at high conversion and high molar yield. Temperature for conversion of the source material 50 is in the range from about 100° C. to about 250° C. In an alternate operation, temperature is selected in the range from 180° C. to about 220° C. at atmospheric pressure. In an alternate operation, temperature for conversion is in the range from about 100° C. to about 180° C. in a partial vacuum of from about from about 20 mm Hg to about 200 mm Hg. Conversion of source material 50 comprising 3-hydroxypropionic acid of at least up to about 90% has been demonstrated with a selectivity of at least up to about 95%. In the instant embodiment, source material 50 was prepared in a water solvent, but is not limited thereto. Other solvents may be used as described herein. In other processes or configurations, solvents are not required. Thus, no limitations are hereby intended.

Figure 3:
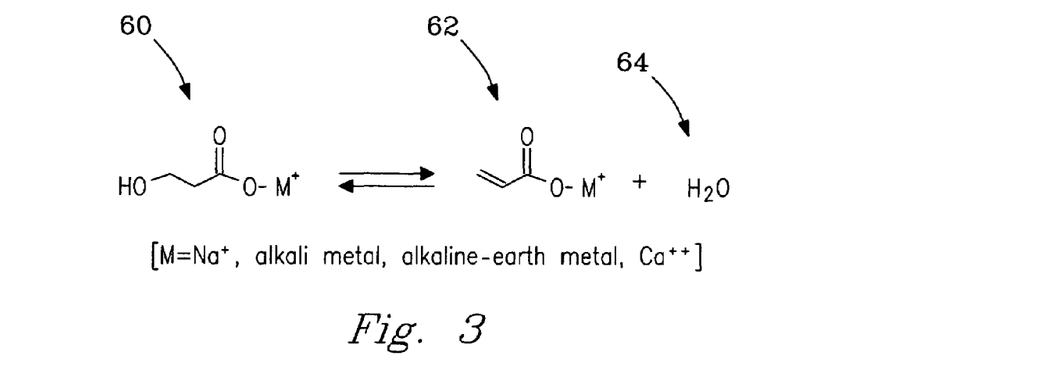
FIG. 3 illustrates a generalized reaction process for conversion a source material comprising salts of β-hydroxy carbonyl compounds including, e.g., alkali metal salts, alkaline earth metal salts, and/or ammonium salts, yielding one or more reaction products selected from acrylate salts (e.g., sodium acrylate, ammonium acrylate), acrylamide, and/or mixtures thereof, according to another embodiment of the invention.

FIG. 3 illustrates a generalized reaction process for conversion of salts of β-hydroxy carbonyl compounds (e.g., alkali metal salts, alkaline earth metal salts, and/or ammonium salts, yielding acrylate salts (e.g., sodium acrylate, ammonium acrylate), acrylamide, and/or mixtures thereof, according to another embodiment of the invention. In the figure, source material 60 comprising, e.g., the sodium salt of 3-hydroxypropionic acid optionally in a solvent is converted via dehydration reaction to a sodium salt of acrylic acid 62 plus water 64 as reaction or conversion product. Various factors effect the conversion of β-hydroxy carbonyl compound salts. For example, under aqueous conditions, dehydration is controlled by reaction equilibria. Such equilibria can require long reaction times permitting concomitant production of acrylate polymers via etherification and/or esterification to occur, a potentially undesirable outcome. Control of reaction conditions, therefore, is important to achieve high conversion of the β-hydroxy carbonyl compound salts forming acrylate salts. In particular, source material 60 can be provided under continuous flow packed with a reaction catalyst, e.g., a fixed-bed reactor configuration, or under batch reaction conditions. Material 60 is heated in the presence of the catalyst at a temperature and residence time sufficient to dehydrate material 60 in contact with the catalyst yielding the desired reaction products 62, e.g., acrylate salts (e.g., sodium acrylate), at high conversion and high molar yield. In one embodiment, temperature for conversion of the source material 60 is in the range from about 100° C. to about 250° C. In another embodiment, temperature for conversion is selected in the range from 180° C. to about 220° C. at atmospheric pressure. In yet another embodiment, temperature for conversion is in the range from about 100° C. to about 180° C. in a partial vacuum in the range from about 20 mm Hg to about 200 mm Hg. No limitations are hereby intended. Conversion of salts of 3-hydroxypropionic acid of up to about 95% has been demonstrated with selectivities to conversion products of up to about 100%. Reaction products can be used as chemical intermediates, or feedstock materials for generating further reaction and conversion products. No limitations are intended.

Conversion of the β-hydroxy carbonyl compound salts provides some potential advantages over conversion of the free acid forms. For example, fermentation processes typically occur under neutral pH conditions yielding 3-hydroxypropionic acid salts, not the free acid. The free acid form of the 3-hydroxypropionic acid and/or of its conversion products can require additional processing steps including, e.g., acidication, separation, and/or removal of the salts, e.g., in a "salt-splitting" step, adding processing costs. To the extent that the salt forms of the conversion product can be used directly in end-use applications, e.g., in formation of super absorbent polymers, conversion of the salts as opposed to the free acid or non-salt forms can minimize separations requirements and/or other associated processing steps. However, no limitations are hereby intended. Reactions that form acrylates or acrylamides can be further optimized in conjunction with use of suitable stabilizing agents or inhibiting agents reducing likelihood of polymer formation. Stabilizing agents and/or inhibiting agents include, but are not limited to, e.g., phenolic compounds (e.g., dimethoxyphenol (DMP) or alkylated phenolic compounds such as di-tert-butyl phenol), quinones (e.g., t-butyl hydroquinone or the monomethyl ether of hydroquinone (MEHQ)), and/or metallic copper or copper salts (e.g., copper sulfate, copper chloride, or copper acetate). Inhibitors and/or stabilizers can be used individually or in combinations as will be known by those of skill in the art. Further, such reagents can be added to the source material, to the catalyst reactor bed, delivered or sprayed onto the walls of the reactor, or be added as a component of a mixture comprising, e.g., 3-hydroxypropionic acid, a catalyst, an inhibitor, and/or other reagent. No limitations are hereby intended. For example, in other embodiments, stabilizing agents and/or inhibiting agents are not used to stabilize the reaction or conversion products. All uses of selected reagents as will be implemented by those of skill in the art are hereby incorporated.

Figure 4:
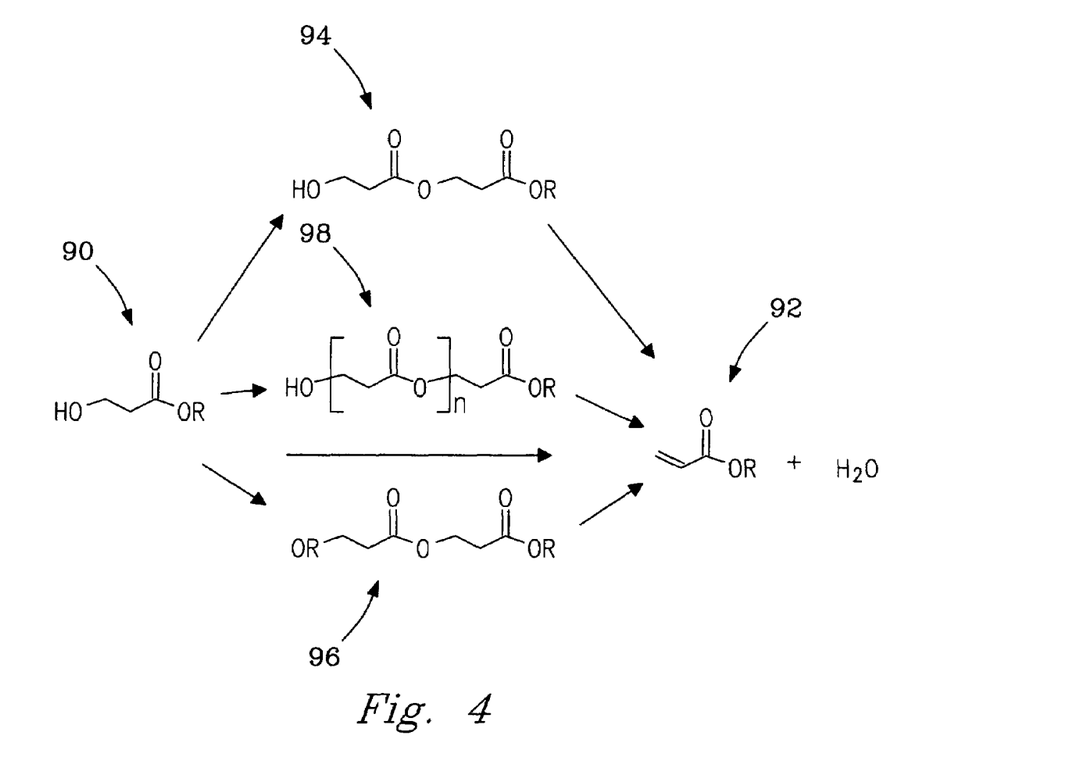
FIG. 4 illustrates various reaction pathways for conversion of a source material comprising salts of 3-hydroxypropionic acid, or the respective free acids, to useful conversion and/or reaction products including, e.g., acrylates, or the corresponding free acids, according to an embodiment of the invention.

FIG. 4 illustrates various reaction pathways for conversion of a source material comprising salts of 3-hydroxypropionic acid 90 (or the respective free acids) to useful conversion and/or reaction products, e.g., acrylates 92 (or the corresponding free acids), according to an embodiment of the invention. In the source material 50, salts of 3-hydroxypropionic acid 90 can dimerize in the reactor yielding, e.g., 3-hydroxypropionic acid acrylate ester dimers 94 and/or 3-hydroxypropionic acid acrylate ether dimers 96, or other oligomeric and/or polymeric species 98 as intermediate and/or end-use conversion products. Experiments detailed in Example 2 below, have demonstrated that despite any potential to form dimers, oligomers, and/or polymeric reaction products, all such moieties convert to desired conversion products, e.g., to useful acrylate salts. For example, results show dimers of 3-hydroxypropionic acid yield reaction products at high conversion and selectivity. Thus, dimeric, oligomeric, and/or polymeric moieties can be used as source materials and can increase the potential applications of the conversion systems described herein. That is, all mixtures and/or combinations of β-hydroxy compounds convert to useful products.

One illustrative system of a commercial-scale design for conversion of salts of source materials comprising β-hydroxy carbonyl compounds, e.g., 3-hydroxypropionic acid, will now be described with reference to FIG. 5.

Figure 5:
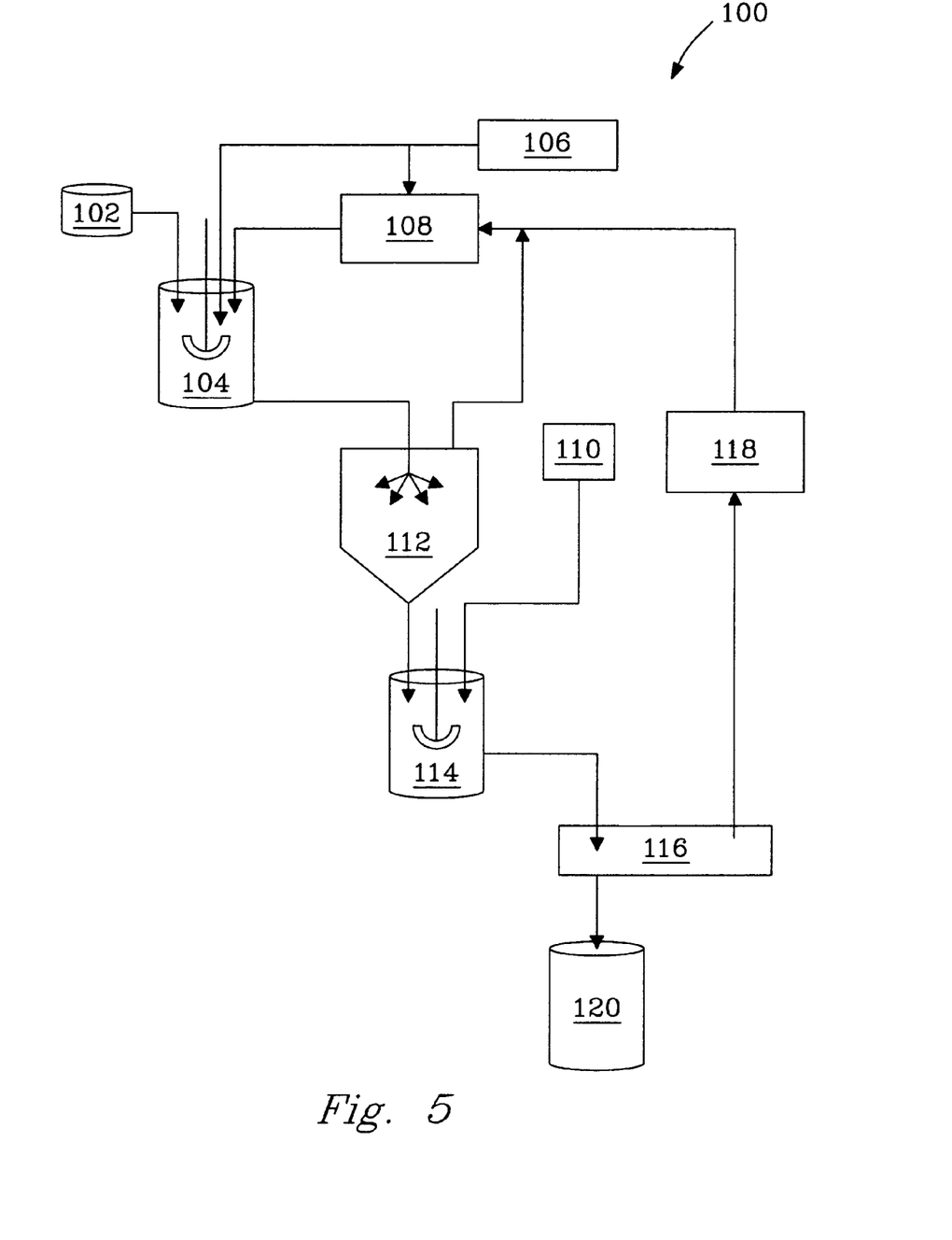
FIG. 5 illustrates a system of a commercial-scale design for conversion of a source material comprising salts of β-hydroxy carbonyl compounds to one or more reaction products, including, e.g., acrylates and acrylamide, according to an embodiment of the invention.

FIG. 5 illustrates a system 100 of a commercial-scale design for conversion of salts of β-hydroxy carbonyl compounds to desirable reaction products, according to an embodiment of the invention. Salts of 3-hydroxypropionic acid, e.g., a sodium or other salt, from source 102 are introduced to mixing tank 104 in a substantially continuous or batch mode operation. A catalyst and/or inhibitor are optionally introduced from inhibitor source 106 and catalyst source 108, respectively. In an alternative mode of operation, source 102 may comprise the source material premixed optionally in water or other solvent for delivery to tank 104. Alternatively, the source material may be provided as a complete mixture (e.g., including catalyst and/or inhibitor) directly to dryer 112. Thus, no limitations are intended. Only partial conversion (~50%) of source material occurs in tank 104, when used, due to reaction equilibria governing conversion in the aqueous medium. However, conversion in the aqueous mixture is rapid and presents a preferred approach when processing time is premium. In addition, greater product selectivity is observed in the aqueous medium, which favors its use, but is not limited thereto. From tank 104, the mixture is next injected into spray dryer 112 which provides heat necessary for removing process water, including water removed from dehydration reactions, and continued dehydration, driving conversion of the 3-hydroxypropionic acid salts to acrylates. In the instant embodiment, spray dryer 112 acts both as an evaporator and dehydration reactor, but is not limited thereto. Reaction products can be separated from the catalyst by injection of water or other solvent. For example, solids from spray dryer 112 are delivered to dissolver tank 114 and water or other solvent is added from, e.g., a solvent source 110, whereby acrylate conversion salts are dissolved in the solvent and catalyst is filtered away in filter tank 116. Recovered catalyst is recycled in tank 118 and re-introduced to source 108 for reuse. Acrylate conversion salts are recovered in storage tank 120.

Figure 6:
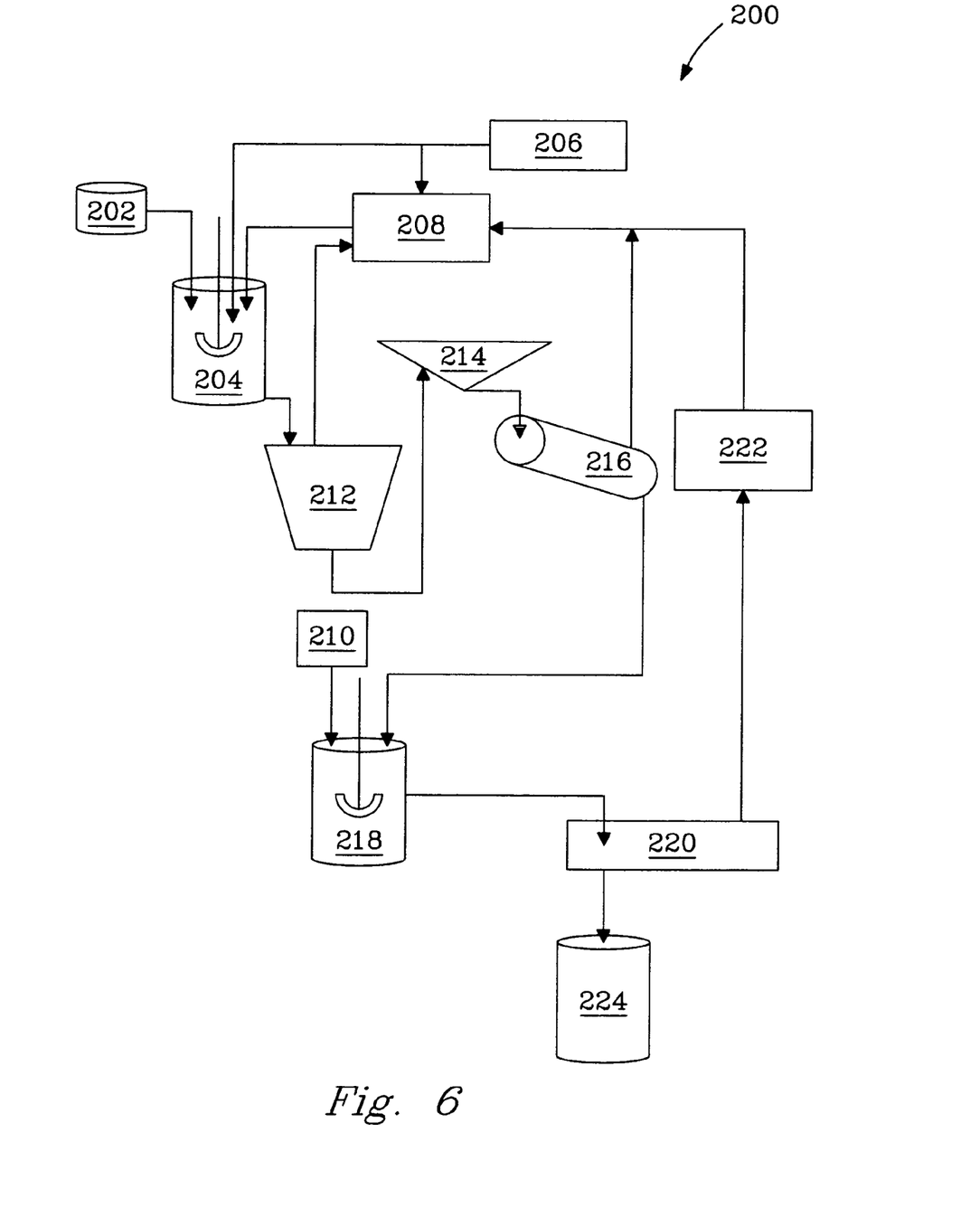
FIG. 6 illustrates a system of a commercial-scale design for conversion of a source material comprising salts of β-hydroxy carbonyl compounds to one or more reaction products, according to another embodiment of the invention.

FIG. 6 illustrates a system 200 of a commercial-scale design for conversion of salts of β-hydroxy carbonyl compounds to desirable reaction products, according to another embodiment of the invention. In an exemplary mode of operation, salts of 3-hydroxypropionic acid, e.g., a sodium or other salt, are provided from source 202 and introduced to mixing tank 204 in a substantially continuous or batch mode operation. A catalyst and/or inhibitor are optionally introduced from inhibitor source 206 and catalyst source 208, respectively. In an alternative mode of operation, source 202 may comprise the source material premixed optionally in water for delivery to tank 204. Alternatively, source material may be provided as a complete mixture (e.g., including catalyst and/or inhibitor) directly to evaporator 212 and delivered to feed hopper 214 where any remaining residual water is removed by introducing solids and/or salt concentrates to a rotary calciner or Auger reactor 216 finalizing conversion of 3-hydroxypropionic acid salts to acrylates. Thus, no limitations are intended. Only partial conversion (~50%) of source material occurs in tank 204, when used, due to reaction equilibria governing conversion in the aqueous medium. However, conversion in the aqueous mixture is highly selective. Thus, partial conversion may be advantageous. The equilibrium mixture from tank 204 is moved into, e.g., an evaporator tank 212 (evaporator) providing heat necessary for removing excess process water. Concentrates or solids from evaporator 212 are delivered to feed hopper 214 where any remaining residual water, including removal of water from dehydration reactions, is removed by introducing solids and/or salt concentrates to a rotary calciner or Auger reactor 216 finalizing conversion of 3-hydroxypropionic acid salts to acrylates.

Acrylate conversion products can be separated from any catalysts when present by injection of water or other solvent. For example, in one approach, solids from rotary calciner or Auger reactor 216 may be delivered to dissolver tank 218 and water or other solvent added from, e.g., a solvent source 210 dissolving the acrylate salts. Catalyst can then be filtered away in filter tank 220, separating the acrylates from the catalyst. Recovered catalyst may be subsequently recycled in tank 222 and re-introduced to source 208 for reuse. Dissolved acrylate salts may then be stored, e.g., as a solution in storage tank 224.

Figure 7:
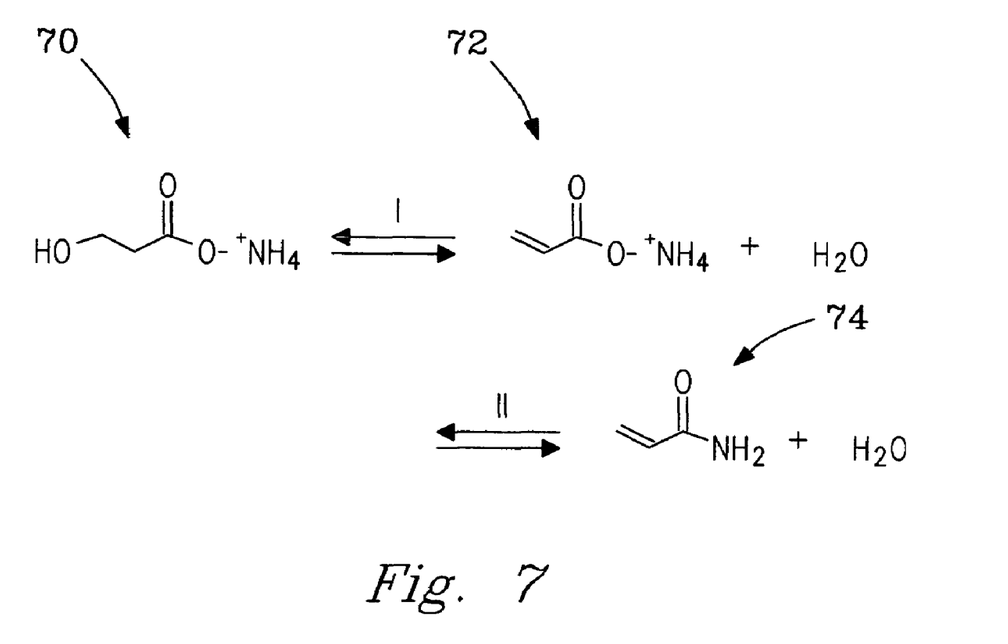
FIG. 7 illustrates a generalized reaction process for conversion of a source material comprising ammonium salts of p-hydroxy carbonyl compounds to one or more reaction products selected from ammonium acrylates, acrylamide, or mixtures thereof, according to an embodiment of the invention.

FIG. 7 illustrates a generalized reaction process for conversion of ammonium salts of β-hydroxy carbonyl compounds including, e.g., the ammonium salt of 3-hydroxypropionic acid 70, to ammonium acrylates 72, acrylamide 74, or mixtures thereof, according to an embodiment of the invention. Dehydration, amidation, and hydrolysis represent three principal reactions illustrated, but are not limited thereto. For example, reaction sequences are immaterial, as dehydration, amidation, and/or hydrolysis reactions can occur simultaneously, consecutively, independently, and/or reversibly, or not at all. In the figure, a single dehydration reaction converts a source material comprising, e.g., the ammonium salt of 3-hydroxypropionic acid 70 to ammonium acrylate 72. Amidation forms acrylamide 74. Conversion can be done catalytically (i.e., in the presence of a reaction catalyst), non-catalytically, or with no additional catalyst added. Products formed, whether, e.g., acrylates (by dehydration) or acrylamide (via amidation) are further controlled by presence and quantity of water and/or ammonia. For example, when greater than one equivalent of ammonia is present, an increase in the yield of acrylamide is effected. Reaction processes are thus tunable to a desired product mix by control of various reaction parameters including, but not limited to, e.g., concentration and temperature.

Figure 8:
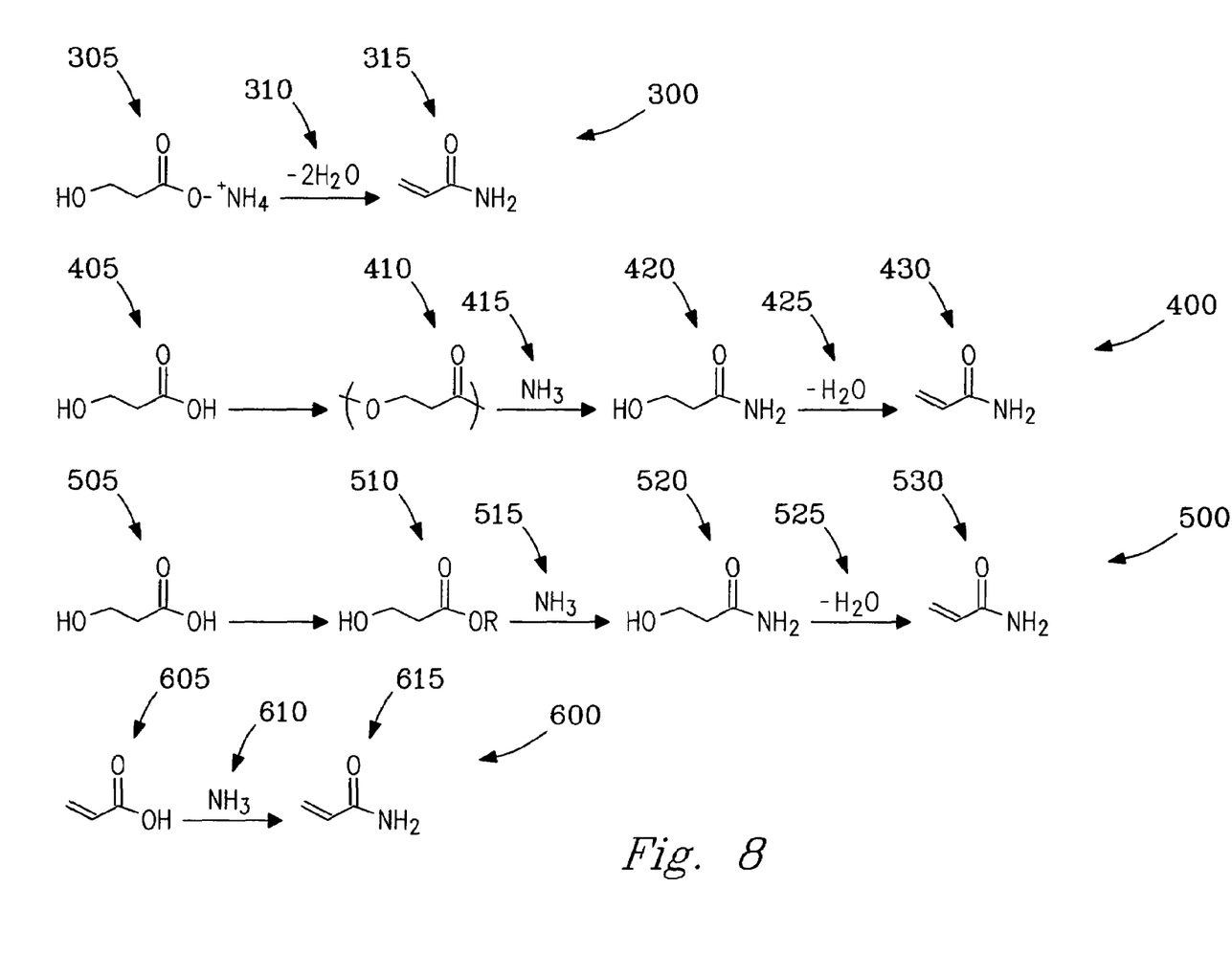
FIG. 8 illustrates various and potentially useful pathways for conversion of a source material comprising β-hydroxy carbonyl compounds or their salts to one or more reaction products.

FIG. 8 illustrates various and potentially useful pathways for conversion of source materials comprising β-hydroxy carbonyl compounds or their salts (e.g., 3-hydroxypropionic acid and 3-hydroxypropionic acid salts) to desirable conversion products. In one reaction pathway 300, illustrated in the figure, the ammonium salt of 3-hydroxypropionic acid 305 can be converted (i.e., by removing water 310) to form acrylamide 315, a useful conversion product.

In another reaction pathway 400, acrylamide 430 can be produced from 3-hydroxypropionic acid 405 via formation of poly- and/or oligo-3-hydroxypropionic acid moieties 410, with subsequent amination using ammonia gas 415 forming an amide 420, followed by dehydration (e.g., either in the presence or absence of dehydration catalysts as disclosed herein) and subsequent loss of water 425.

In another reaction pathway 500, acrylamide 530 can be produced in a reaction process involving esterification of terminal —OH groups of a source material comprising 3-hydroxypropionic acid 505 using reagents known in the art, including, but not limited to, e.g., alkanols composed of from 1 to 20 carbon atoms (e.g., methanol, dodecanol, etc), yielding various 3-hydroxypropionic acid esters 510. For example, methanol as a substitution reagent yields a $C_1$ (i.e., methyl) R-substituted ester; dodecanol as a substitution reagent yields a $C_{12}$ (i.e., dodecyl) R-substituted ester. Subsequent amidation of the esterified 3-hydroxypropionic acid moieties 510 using $NH_3$ 515 yields free amide 520 moieties. Dehydration of the amide 520 and loss of water 525 yields the free acrylamide 530.

In another reaction pathway 600, acrylamide 615 can be produced by amidation of acrylic acid 605 using $NH_3$ 610.

All conversion pathways as will be implemented by those of skill in the art are encompassed herein. No limitations are hereby intended.

The following examples are intended to promote a further understanding of the present invention.

EXAMPLES

Example 1 details catalytic conversion of 3-hydroxypropionic acid in the presence of a reaction catalyst forming acrylic acid in either a continuous or a batch mode of operation. Example 2 details catalytic conversion of ammonium salts of 3-hydroxypropionic acid forming tunable mixtures of various conversion products. Example 3 details conversion of source material both with and without catalysts in a continuous mode of operation for extended periods with productive yields of conversion products. Example 4 details catalytic conversion of sodium salts of 3-hydroxypropionic acid in a batch mode of operation forming important conversion products.

Example 1

Example 1 describes catalytic conversion of 3-hydroxypropionic acid in the presence of a reaction catalyst forming acrylic acid in a continuous mode of operation. In one exemplary test, system 10 was configured as follows: a 12.2 wt % source material comprising β-hydroxy carbonyl compounds (including, e.g., 9.19 wt % 3-hydroxypropionic acid, 1.22 wt % 3-hydroxypropionic acid ether dimers, and 1.48 wt % 3-hydroxypropionic acid ester dimers) was prepared in water. Catalyst reactor 12 was packed with 5.9 g of a 16-30 mesh titanium catalyst, e.g., Ti-0720® (Engelhard Corp., Iselin, N.J.). Source material was fed to reactor 12 from source 14 at a rate of about 0.2 WHSV at a temperature of about 180° C. Samples were collected in approximately one hour increments for 44 hours. Total source material delivered to reactor 12 was 69.13 g. Samples were analyzed by HPLC for acrylic acid, 3-hydroxypropionic acid, and other potential byproducts, and results for conversion and selectively were calculated using equations [1] and [2]. Quantity of product recovered, by weight, were determined to be 1.20 g 3-hydroxypropionic acid (residual source material) and 54.00 g acrylic acid. Results showed a total conversion of 3-hydroxypropionic acid of 98.3%. Acrylic acid selectivity was 99.4%. Total molar recovery (molar balance) of acrylic acid was 99.4%. Results further showed the titania catalyst had no detectable decrease in activity, indicating a long potential lifetime, e.g., up to one year. Results further showed any dimers of 3-hydroxypropionic acid present in the source material or inadvertently formed during processing were converted to acrylic acid, the desired end product. Thus, dimers can also be considered valuable feedstock materials rather than low-value byproducts.

In another test, a higher flow rate (0.4 WHSV) with an 8.8 wt % source material at a temperature in the range between about 180° C. and 190° C. provided a similar selectivity and conversion. Results showed a conversion for 3-hydroxypropionic acid of about 100 percent, with a molar selectivity for acrylic acid of about 100 percent. Mass balances (~100%) were also achieved while total weight balances were consistently only slightly lower (~95% to 98%) indicating only water was lost from the product receiver. Results further show no byproducts were detected by HPLC.

As discussed herein, conversion of 3-hydroxypropionic acid source material in an aqueous medium is subject to reaction equilibria, which can be controlled by removing various reaction products (e.g., acrylic acid and/or water) from the reactive medium in reactor 12. For example, conversion products are generally volatile and can be removed from the gas stream, further driving the conversion reaction thereby controlling and/or limiting further reactions and/or chemistries including, but not limited to, e.g., dimerization, oligomerization, re-hydration. In addition, flow rates and temperatures can be selected that optimize reactor conditions. No limitations are intended.

Example 2

Example 2 details catalytic conversion of ammonium salts of 3-hydroxypropionic acid in a continuous mode of operation producing ammonium acrylates and/or easily separable mixtures of ammonium acrylates plus acrylamide on a commercial scale.

In an exemplary test, system 10 was configured as follows. An 8.62 wt % source material comprising ammonium salts of 3-hydroxypropionic acid was prepared in water. Reactor 12 was packed with 5.8 g of titanium catalyst, e.g., Ti-0720® (Engelhard Corp., Iselin, N.J.). Source material was introduced to reactor 12 from source 14 at a flow rate of about 0.2 (WHSV) at a temperature of about 180° C. Samples were collected in approximately one hour increments for a total of about 37 hours. Total source material delivered to the reactor was 41.43 g. Samples were analyzed by HPLC for acrylic acid, 3-hydroxypropionic acid, acrylamide, and other potential byproducts, and results for conversion and selectively were calculated. Quantity of products recovered, by weight, was determined to be 21.49 g acrylic acid (as acrylates), 0.49 g acrylamide, and 2.45 g 3-hydroxypropionic acid (unreacted source material). Total conversion of the source material was 94%. Molar recovery was 72%. Molar yield of acrylic acid was 65%. Molar yield of acrylamide was 1.5%. Test results indicate a continuous reactor can be operated for extended periods without a decrease in productive yields. Addition of acrylamide and/or acrylic acid stabilizers can be expected to enhance the product yields.

In another test, a 10.1% source material comprising ammonium salts of 3-hydroxypropionic acid was reacted at a temperature of about 240° C. in the presence of a silica-alumina catalyst (Si/Al T-869, Süd-Chemie AG, Bruckmühl GE). Total conversion was 68%, with a selectivity to acrylates of 80%.

In another test, a source material comprising 3-hydroxypropionic acid amide (5 wt % in water) was introduced at a flow rate of about 0.1 WHSV. Results showed a selectivity of 67% to acrylate and a selectivity of 1.8% to acrylamide, indicating that hydrolysis reactions can occur through control of water concentration.

In another test, designed to show acrylamide can be formed from aqueous solutions of the source material comprising ammonium salts of 3-hydroxypropionic acid, an 8.7 wt % source material solution (comprising 27.73 g of ~15 wt % ammonium salt of 3-hydroxypropionic acid in water with 20.55 g concentrated ammonium hydroxide added) in the reactor. Ammonium hydroxide was added to simulate ammonia vapor phase pressure in the reactor 12. Reactor 12 was packed with 5.71 g Ti-0720® (Engelhard) catalyst. Temperature was selected in the range from about 200° C. and about 250° C. Collected samples were analyzed by HPLC for acrylic acid (present as ammonium acrylates), 3-hydroxypropionic acid, and acrylamide. Results showed a significant quantity of the desired acrylamide product was formed (about 25%). Test further showed production of ammonium acrylates as a co-product at a molar yield of about 75%. Results are significant as they show acrylamide is produced in the instant process from an aqueous solution of the source material comprising the ammonium salt of 3-hydroxypropionic acid. Constant removal of the acrylamide product recovered provides a way to inhibit polymerization of the acrylamide under long reaction times. Hence, virtually the entire source material is converted to desirable products. Altering the water ratio and/or varying the ammonia pressure (e.g., using a direct ammonia gas feed at greater than atmospheric pressure), the ratio of acrylate to acrylamide can be expected to improve, providing options for tuning the reactor to achieve various desired ratios of the reaction products. No limitations are hereby intended.

Amide hydrolysis tends to occur in the absence of ammonia gas. In contrast, when ammonia is present, a dramatic increase in conversion of 3-hydroxypropionic acid salts to acrylamide occurs. Expectation is that optimum yields will be achieved through use of stabilizing agents, as described hereinabove. Results may be further optimized for conversion, yields, or recovery of products, through such conditions as temperature, water concentrations (e.g., up to about 80%), reactants (3-hydroxypropionic acid salts and acrylate salts), and ammonia gas pressure thereby optimizing yields of ammonium acrylate, acrylamide, and/or tunable mixtures thereof.

However, tests demonstrate the propensity for good outcomes using various conditions and parameters described herein, in particular, when optimized for the product of interest, as will be understood by those of skill in the art. Although some mass balance issues must be tackled when operating under extended reaction periods, the robustness of a continuous reactor has been demonstrated.

In sum, dehydration is required for conversion of ammonium salts of 3-hydroxypropionic acid to acrylamide via dehydration of the β-hydroxy group and amidation of the acid functionality. Formation of 3-hydroxypropionic acid amide followed by reactive distillation to acrylamide presents a plausible clean route to acrylamide. However, dehydration of the β-hydroxy functionality is at least competitive with amidation and hence direct amidation of acrylate is something to be considered. Another route for conversion of ammonium salts of 3-hydroxypropionic acid is via esterification, e.g., using an alcohol (e.g., R—OH), followed by aminolysis to yield the 3-hydroxypropionic acid amide (i.e., acrylamide).

Example 3

Example 3 details conversion of salts of 3-hydroxypropionic acid without additional catalyst added. In an exemplary test, system 10 was configured as follows. Reactor 12 was packed with 5.51 g of crushed quartz glass in place of a catalyst. An 8.86 wt % aqueous source material comprising an ammonium salt of 3-hydroxypropionic acid was employed. Temperature of operation was 180° C. Flow rate was 0.2 (WHSV), based on quantity of quartz glass used. Reactor 12 was operated for a period exceeding 36 hours (~2207 minutes). In the absence of added catalyst, results showed an 84.4% conversion, a selectivity for acrylates of 71.9%, with an overall molar yield of acrylates of about 60% from ammonium 3-hydroxypropionate. Ammonia may play a potential role as a catalyst in the conversion process. Catalysts, including, e.g., basic catalysts, may further offer at least some limited improvement in conversion of ammonium salts of 3-hydroxypropionic acid to acrylates, but the invention is not limited thereto, as described and demonstrated herein. When utilized, choice for selected catalyst is not limited. For example, acidic catalysts can be completely defunctionalized in the presence of basic ammonia. Thus, basic catalysts may prove more beneficial in selective conversion and yields.

Example 4

Example 4 details conversion of salts of 3-hydroxypropionic acid forming important conversion products, including, but not limited to, acrylates. The term "melt" or as used herein describes the state of a source material introduced to a reactor at a temperature near, greater than, or equal to the melting point temperature. In exemplary tests, the sodium salt of 3-hydroxypropionic acid was mixed with a dehydration catalyst, e.g., Zr(OH)$_4$, prepared internally, and a polymer inhibitor, e.g., 2,6 dimethoxyphenol (DMP) (Sigma-Aldrich, St. Louis, Mo.) in a 1:1:1 (salt:catalyst:inhibitor) weight ratio and melted in vials in a batch reactor open to air atmosphere at 200° C. for 1, 2, 3, and 4 hours, respectively. Zr(OH)$_4$ was prepared via ammonium hydroxide precipitation of zirconyl nitrate (Spectrum Chemicals, Gardena, Calif.) followed by drying in a vacuum oven at 50° C. Quantity of conversion products was determined by HPLC. Results are tabulated in Table 1.

TABLE 1

Yields for sodium acrylate formed in batch mode under catalytic conditions from a source material comprising a 1:1:1 weight ratio of a sodium salt of 3-hydroxypropionic acid (3HP), a dehydration catalyst Zr(OH)$_4$, and 2,6 dimethoxyphenol (DMP) polymer inhibitor.

| Run | Conditions | Analyte | Mole % | Conversion | Selectivity |
|---|---|---|---|---|---|
| 1 | Na3HP | Na3HP | 14.3 | 85.7 | 85.4 |
|   | Zr(OH)$_4$ | NaAcrylate | 73.2 | | |
|   | DMP* | Dimer | 3.4 | | 89.4** |
|   | 1 hour | Polymer | 9.1 | | |
|   |   | Mass Balance (wt %): | 101.2 | | |
| 2 | Na3HP | Na3HP | 13.6 | 86.4 | 79.8 |
|   | Zr(OH)$_4$ | NaAcrylate | 68.9 | | |
|   | DMP* | Dimer | 3.4 | | 83.8** |
|   | 2 hour | Polymer | 14.0 | | |
|   |   | Mass Balance (wt %): | 102.4 | | |
| 3 | Na3HP | Na3HP | 11.8 | 88.2 | 74.2 |
|   | Zr(OH)$_4$ | NaAcrylate | 65.4 | | |
|   | DMP* | Dimer | 3.8 | | 78.5** |
|   | 3 hour | Polymer | 19.0 | | |
|   |   | Mass Balance (wt %): | 100.8 | | |
| 4 | Na3HP | Na3HP | 10.5 | 89.5 | 69.1 |
|   | Zr(OH)$_4$ | NaAcrylate | 61.8 | | |
|   | DMP* | Dimer | 3.8 | | 73.3** |
|   | 4 hour | Polymer | 23.8 | | |
|   |   | Mass Balance (wt %): | 103.4 | | |

*DMP = 2,6 dimethoxyphenol.
**Selectivity if ether dimers are converted.

Results for tests 1 through 4 showed an 86% conversion with 90% selectivity to sodium acrylate within 1 hour. Only slight increases in conversion were obtained at periods longer than 1 hour. Mass balances were approximately 100%. Results further showed that while dimers (e.g., ether and ester dimers of 3-hydroxypropionic acid) and polymers form during heating, these moieties are still converted to acrylate products. Rates for conversion of ether dimers and ester dimers to acrylates are lower than for conversion of 3-hydroxypropionic acid monomer.

In other melt tests using ECS-3® catalyst (Engelhard, Iselin N.J.), after 2 hours, combined yield of sodium acrylate and polymer was 91.2%, with a 94.5% conversion and a sodium acrylate selectivity of 96.4%.

Conversions in comparable aqueous preparations, which are equilibrium controlled, were about 50% of those involving melts with about 100% selectivity. Reactions proceed approximately halfway forming sodium acrylate exclusively, i.e., no polymer or ether dimer are formed. That reactions may be equilibrium-controlled should not be considered a limitation of the present invention, as optimum conversion of source materials has been demonstrated by various means including, e.g., selectively removing reaction products as they are formed. Further, in processes described herein in reference to FIG. 5 and FIG. 6, for example, differences observed for aqueous and melt tests may be applied in commercial-scale applications by, e.g., sequentially combining both the solution phase and solid state aspects in processes. Conversions and selectivities higher than those from the individual processes are conceivable. For example, in the aqueous medium, 50% conversion of salts of 3-hydroxypropionic acid is achieved at ~100% selectivity (no polymer or ether dimer are formed). Water can then be removed and the conversion reactions resumed in the solid state. For this phase, conversion and selectivities of greater than about 95% may be expected. Further, given the lower quantity of material remaining to be converted in the solid phase, reaction times may be further enhanced. Further improvements in yield may be obtained using shorter residence times at higher temperatures. Sodium acrylate is often sold commercially as an aqueous solution. Hence, to provide the aqueous solution in a commercial process, separation, e.g., of the recovered product and catalyst, can be achieved simply by dissolving the acrylate products in water and filtering the catalyst. All configurations as will be envisioned by those of skill in the art are within the scope of the invention.

Those of skill in the art will recognize that other suitable catalysts may be selected as described herein. No limitations are intended. For example, catalysts selected from among the various weak or strong acids, acidic catalysts and materials (e.g., acidic resins), or basic catalysts and materials, including solid acids and bases may be employed. In addition, solid catalysts will provide ease of product and catalyst separation. Thus, no limitations are hereby intended.

While the preferred embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

We claim:

1. A process for converting a β-hydroxy carbonyl compound salt to a product salt, characterized by the step of:
dehydrating a β-hydroxy carbonyl compound salt in a non-aqueous state at a preselected conversion temperature to produce a product salt selected from the group consisting of acrylate salts, polymer salts thereof, and combinations thereof at a yield that exceeds an aqueous equilibrium-controlled maximum, wherein said process is conducted in melt form in the presence of a polymerization inhibitor.

2. The process of claim 1, wherein the step of dehydrating said β-hydroxy carbonyl compound salt includes dehydrating a melt or a solid of said salt.

3. The process of claim 1, wherein said β-hydroxy carbonyl compound salt is selected from the group consisting of alkali salts, alkaline earth salts, transition metal salts, precious metal salts, ammonium salts, and combinations thereof.

4. The process of claim 1, wherein said β-hydroxy carbonyl compound salt is selected from the group consisting of 3-hydroxypropionate salts, 3-hydroxypropionate ester dimer salts, 3-hydroxypropionate ether dimer salts, and combinations thereof.

5. The process of claim 1, wherein the step of dehydrating said β-hydroxy carbonyl compound salt includes dehydrating said salt in the presence of a dehydration catalyst.

6. The process of claim 5, wherein said dehydration catalyst is selected from the group consisting of solid oxide catalysts, solid acid catalysts, acidic catalysts, weakly acidic catalysts, strongly acidic catalysts, basic catalysts, ion-exchange resins, acidic gases, basic gases, and combinations thereof.

7. The process of claim 6, wherein said solid oxide catalysts are selected from the group consisting of $TiO_2$, $ZrO_2$, $Al_2O_3$, $SiO_2$, $ZnO_2$, $SnO_2$, $WO_3$, $MnO_2$, $Fe_2O_3$, $SiO_2/Al_2O_3$, $ZrO_2/WO_3$, $ZrO_2/Fe_2O_3$, $ZrO_2/MnO_2$, and combinations thereof.

8. The process of claim 6, wherein said acidic or weakly acidic catalysts are selected from the group consisting of titanic acids, metal oxide hydrates, metal sulfates, metal oxide sulfates, metal phosphates, metal oxide phosphates, carbon dioxide, mineral acids, carboxylic acids, acidic resins, acidic zeolites, clays, ammonium salts thereof, and combinations thereof.

9. The process of claim 6, wherein said acidic catalysts are selected from the group consisting of titania catalysts, $SiO_2/H_3PO_4$ catalysts, fluorinated $Al_2O_3$ catalysts, $Nb_2O_3/PO_4^{-3}$ catalysts, $Nb_2O_3/SO_4^{-2}$ catalysts, $Nb_2O_5 \cdot H_2O$ catalysts, phosphotungstic acid catalysts, phosphomolybdic acid catalysts, silicomolybdic acid catalysts, silicotungstic acid catalysts, carbon dioxide, acidic polyvinylpyridine hydrochloride catalysts, hydrated acidic silica catalysts, and combinations thereof.

10. The process of claim 6, wherein said basic catalysts are selected from the group consisting of ammonia, polyvinylpyridine catalysts, metal hydroxides, $Zr(OH)_4$ catalysts, or amines of the form $NR_1R_2R_3$, wherein $R_1$, $R_2$, and $R_3$ are functional groups independently selected from the group consisting of H, hydrocarbons containing from 1 to 20 carbon atoms, heteroatom substituted hydrocarbons containing from 1 to 20 carbon atoms, alkyl and/or aryl groups containing from 1 to 20 carbon atoms, and combinations thereof.

11. The process of claim 1, wherein the step of dehydrating said β-hydroxy carbonyl compound salt includes removing water to obtain said product salt.

12. The process of claim 1, wherein the step of dehydrating said β-hydroxy carbonyl compound salt in said non-aqueous state is preceded by the step of dehydrating said β-hydroxy carbonyl compound salt in an aqueous state to achieve an aqueous state equilibrium controlled maximum yield.

13. The process of claim 12, wherein any of the steps of dehydrating said β-hydroxy carbonyl compound salt include use of a reactor selected from the group consisting of: calciners; extruders; evaporators; evacuaters; Auger reactors; fluidized bed reactors; and combinations thereof.

14. The process of claim 13, further comprising including the step of rehydrating said product salt in water for recovery thereof.

15. The process of claim 12, wherein the step of dehydrating said β-hydroxy carbonyl compound salt in said aqueous state that precedes the step of dehydrating in said non-aqueous state includes spray drying to move beyond said aqueous state equilibrium controlled maximum yield.

16. The process of claim 1, wherein about 60 percent to about 100 percent of said β-hydroxy carbonyl compound salt is converted to said product salt.

17. The process of claim 1, wherein said yield of said product salt is a molar yield that is in the range from about 70% to about 100%.

18. The process of claim 1, wherein the step of dehydrating said β-hydroxy carbonyl compound salt is performed at a preselected conversion temperature that is in the range from about 100° C. to about 250° C.

19. The process of claim 1, wherein the step of dehydrating said β-hydroxy carbonyl compound salt is performed at a preselected conversion temperature that is in the range from about 180° C. to about 220° C. at atmospheric pressure.

20. The process of claim 1, wherein the step of dehydrating said β-hydroxy carbonyl compound salt is performed at a preselected conversion temperature that is in the range from about 100° C. to about 180° C. with a partial vacuum that is in the range from about 20 mm Hg to about 200 mm Hg.

21. The process of claim 12, wherein at least one of the steps of dehydrating said β-hydroxy carbonyl compound salt is performed in the presence of a dehydration catalyst.

22. The process of claim 1, wherein the step of removing water to obtain said product salt includes use of a reactor selected from the group consisting of: calciners; extruders; evaporators; evacuators; Auger reactors; fluidized bed reactors, and combinations thereof.

23. The process of claim 1, further including the step of rehydrating said product salt in water for recovery thereof.

* * * * *